Figure 1:
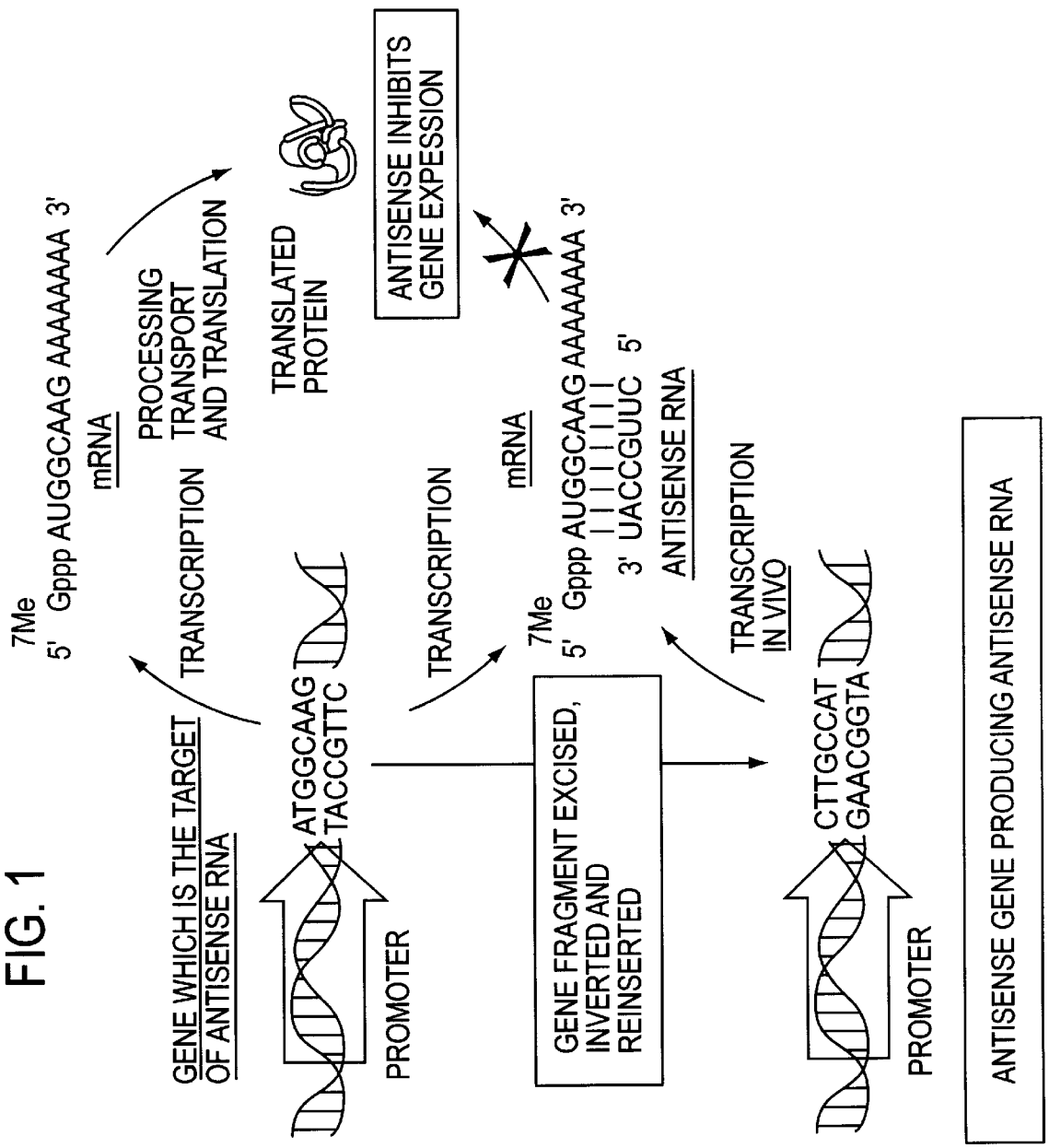

United States Patent [19]
Hofvander et al.

[11] Patent Number: 5,856,467
[45] Date of Patent: Jan. 5, 1999

[54] GENETICALLY ENGINEERED MODIFICATION OF POTATO TO FORM AMYLOSE-TYPE STARCH

[75] Inventors: Per Hofvander, Falsterbo; Per T. Persson, Kristianstad; Anneli Tallberg, Lund; Olle Wikstrom, Kristianstad, all of Sweden

[73] Assignee: Amylogene HB, Svalöv, Sweden

[21] Appl. No.: 471,965

[22] Filed: Jun. 6, 1995

Related U.S. Application Data

[62] Division of Ser. No. 70,426, filed as PCT/SE91/00891 Dec. 20, 1991.

[30] Foreign Application Priority Data

Dec. 21, 1990 [SE] Sweden .................................. 9004095

[51] Int. Cl.$^6$ .................................................. C08B 33/00
[52] U.S. Cl. .......................... 536/45; 536/23.6; 536/24.5; 536/102; 800/205
[58] Field of Search ........................... 536/45, 24.5, 102; 536/23.6; 800/205

[56] References Cited

U.S. PATENT DOCUMENTS

| | | |
|---|---|---|
| 4,723,052 | 2/1988 | Cochran . |
| 5,047,373 | 9/1991 | Joyce . |

FOREIGN PATENT DOCUMENTS

| | | |
|---|---|---|
| 0 335 451 | 10/1989 | European Pat. Off. . |
| 0 368 526 | 5/1990 | European Pat. Off. . |

OTHER PUBLICATIONS

"Isolation of a Q–Enzyme with M, 103 000 From Potato Tubers", Phytochemistry, vol. 30, No. 2, pp. 437–444, (1991), Andreas Blennow and Göte Johansson.

"Immunological Comparison of the Starch Branching Enzymes from Potato Tubers and Maize Kernels", Plant Physiology, vol. 90, (1989), pp. 75–84, Greetje H. Vos–Scheperkeuter, et al.

"Structural and Functional Analysis of Two Waxy Gene Promoters from Potato", W. Rohde et al., J. Genet. & Breed. 44:311–315, (1990).

"Antisense RNA inhibition of Polygalacturonase Gene Expression in Transgenic Tomatoes", C.J.S. Smith et al., *Nature,* Letters to Nature, vol. 334, Aug. 25, 1988, pp. 724–726.

"Organ–Specific Gene Expression in Potato: Isolation and Characterization of Tuber–Specific cDNA Sequences", S. Rosahl et al., *Molecular Gen Genet,* (1986) 202: pp. 368–373.

"Cloning and Expression Analysis of a Potato cDNA that Encodes Branching Enzyme: Evidence for Co–expression of Starch Biosynthetic Genes", Jens Kossmann et al., *Molecular Gen Genet,* (1991) 230: pp. 39–44.

Hovenkamp–Hemelink et al., Theoretical and Applied Genetics, vol. 75, pp. 217–221, (1987).

*Primary Examiner*—James O. Wilson
*Attorney, Agent, or Firm*—Burns, Doane, Swecker & Mathis, L.L.P.

[57] ABSTRACT

Genetically engineered modification of potato for suppressing formation of amylopectin-type starch is described.

The invention describes an antisense construct for inhibiting, to a varying extent, the expression of the gene coding for formation of branching enzyme (BE gene) in potato, said antisense construct comprising a tuber-specific promoter, transcription start and the first exon of the BE gene, inserted in the antisense direction.

Also cells, plants, tubers, microtubers and seeds of potato comprising said antisense construct are described.

Finally, amylose-type starch, both native and derivatized, derived from the potato that is modified in a genetically engineered manner, as well as a method of suppressing amylopectin formation in potato are described.

10 Claims, 2 Drawing Sheets

GENETICALLY ENGINEERED MODIFICATION OF POTATO TO FORM AMYLOSE-TYPE STARCH

This application is a divisional of application Ser. No. 08/070,426, filed Nov. 24, 1993, which corresponds to PCT/SE91/00891, filed Dec. 20, 1991.

The present invention relates to genetically engineered modification of potato, resulting in the formation of an increasing amount of amylose-type starch as compared to amylopectin-type starch in the potato. The genetically engineered modification implies the insertion of a gene fragment into potato, said gene fragment comprising transcription start and a part of the gene coding for the formation of branching enzyme (BE gene) in potato, inserted in the antisense direction, together with a tuber-specific promoter.

BACKGROUND OF THE INVENTION

Starch in various forms is of great import in the food and paper industry. In the future, starch will also be a great potential for producing polymers which are degradable in nature, e.g. for use as packing material. Many different starch products are known which are produced by derivatization of native starch originating from, inter alia, maize and potato. Starch from potato and maize, respectively, is competing in most market areas.

In the potato tuber, starch is the greatest part of the solid matter. About ¼ to ⅕ of the starch in potato is amylose, while the remainder of the starch is amylopectin. These two components of the starch have different fields of application, and therefore the possibility of producing either pure amylose or pure amylopectin is most interesting. The two starch components can be produced from common starch, which requires a number of process steps and, consequently, is expensive and complicated.

It has now been proven that by genetic engineering it is possible to modify potato so that the proportion between the two starch components amylose and amylopectin changes in the actual tubers. As a result, a starch quality is obtained which can compete in the areas where potato starch is normally not used today. Starch From such potato which is modified in a genetically engineered manner has great potential as a food additive, since it has not been subjected to any, chemical modification process.

Starch Synthesis

The synthesis of starch and the regulation thereof are presently being studied with great interest, both on the level of basic research and for industrial application. Although much is known about the assistance of certain enzymes in the transformation of saccharose into starch, the biosynthesis of starch has not yet been elucidated. By conducting research above all into maize, it has, however, been possible to elucidate part of the routes of synthesis and the enzymes participating in these reactions. The most important starch-synthesizing enzymes for producing the starch granules are starch synthase and branching enzyme. In maize, three forms of starch synthase have so far been demonstrated and studied, two of which are soluble and one is insolubly associated with the starch granules. Also branching enzyme in maize consists of three forms which are probably coded by three different genes.

Branching Enzyme in Different Plant Species

The starch granules contain a mixture of linear and branched molecules which form the starch components amylose and amylopectin. Amylopectin is produced by interaction between starch synthase and branching enzyme, alpha-1,4-glucane; alpha-1,4-glucane-6-glucosyl transferase (EC 2.4.1.18). Branching enzyme (BE) hydrolyses alpha-1,4 bonds and synthetises alpha-1,6 bonds (Mac Donald & Preiss, 1985; Preiss, 1988).

Endosperm of normal maize contains three forms of BE protein, designated BE I, BE IIa and BE IIb. The mutation amylose extender (amylose extender) inhibits the activity of the enzyme BE IIb, which results in a reduced content of amylopectin and a corresponding increase of the amylose content. ae endosperm thus has a different proportion of amylose to amylopectin than normal maize, viz. 65:35 instead of 25:75 (De Vries Kuranda, 1987).

Although the similarities between the three enzyme forms are great, each of them has properties in its primary structure which make them unique. The genes for each enzyme form have not been identified so far, but by isolation of cDNA clones for each BE form, each gene can in all probability be characterized.

In normal pea, two forms of branching enzyme (BE) have been identified. A mutation in r locus, which results in a creased pea, affects the activity of BE, thereby inhibiting one enzyme form. This results in a modified composition of the starch with 30% amylopectin and 70% amylose, as compared to the reversed proportion in round normal pea (Smith, 1988).

Branching enzyme (BE) in potato is a monomer protein, i.e. it is a single enzyme form. The molecular weight of potato BE varies between 79 and 103 kD, depending on the purifying process used. There are indications that potato BE should consist of several forms, but presumably several forms are degradation products from the actual protein (Vos-Scheperkeuter, 1989; Blennow & Johansson, 1990).

Peptide sequencing of three BE forms, separated by electrophoresis, has such great homology between the enzyme forms that these are assumed to have the same origin. Serological tests support this assumption, since antisera from the three enzyme forms cross-react with each other.

Inhibition of Branching Enzyme

By inhibiting one of the forms of branching enzyme in maize and pea, the composition of the starch changes so that the content of amylose increases strongly at the sacrifice of the amylopectin production.

In potato, a natural genotype with an increased content of amylose has not been found so far. However, it is possible to reduce the content of BE to a varying extent, which results in the starch in the potato tuber having increased content of amylose as compared to common potato.

The reduction of the formation of enzyme can be accomplished in several ways, e.g. by:

mutagen treatment which results in a modification of the gene sequence coding for the formation of the enzyme incorporation of a transposon in the gene sequence coding for the enzyme genetically engineered modification so that the expression of the gene coding for the enzyme is modified by so-called antisense gene inhibition.

FIG. 1 illustrates a specific suppression of normal gene expression in that a complementary antisense nucleotide is allowed to hybridize with mRNA for a target gene. The antisense nucleotide thus is antisense RNA which is transcribed in vivo from a "reversed" gene sequence (Izant, 1989).

By using the antisense technique, various gene functions in plants have been inhibited. The antisense construct for chalcone synthase, polygalacturonase and phosphinotricin acetyltransferase has been used to inhibit the corresponding enzyme in the plant species petunia, tomato and tobacco (Van der Krol et al, 1990; Sheehy et al, 1988; Cornelissen, 1989).

The object of the invention is to provide a varyingly increased amylose production in potato tuber by using antisense gene inhibition.

SUMMARY OF THE INVENTION

According to the invention the function of the BE gene and, thus, the amylopectin production in potato are inhibited to a varying extent by using new antisense constructs. The antisense constructs according to the invention comprise a tuber-specific promoter, transcription start and the first exon of the gene coding for formation of branching enzyme (BE gene) in potato, inserted in the antisense direction.

The invention also comprises a gene coding for formation of branching enzyme in potato, the so-called BE gene.

The invention further comprises vectors including the antisense constructs according to the invention.

In further aspects, the invention comprises cells, plants, tubers, microtubers and seeds, whose genome contains the antisense constructs according to the invention.

In still further aspects, the invention comprises amylose-type starch, both native and derivatized.

Finally, the invention comprises a method of suppressing formation of amylopectin-type starch in potato, whereby the potato tubers form a varyingly increased amount of amylose-type starch.

Figure 2:
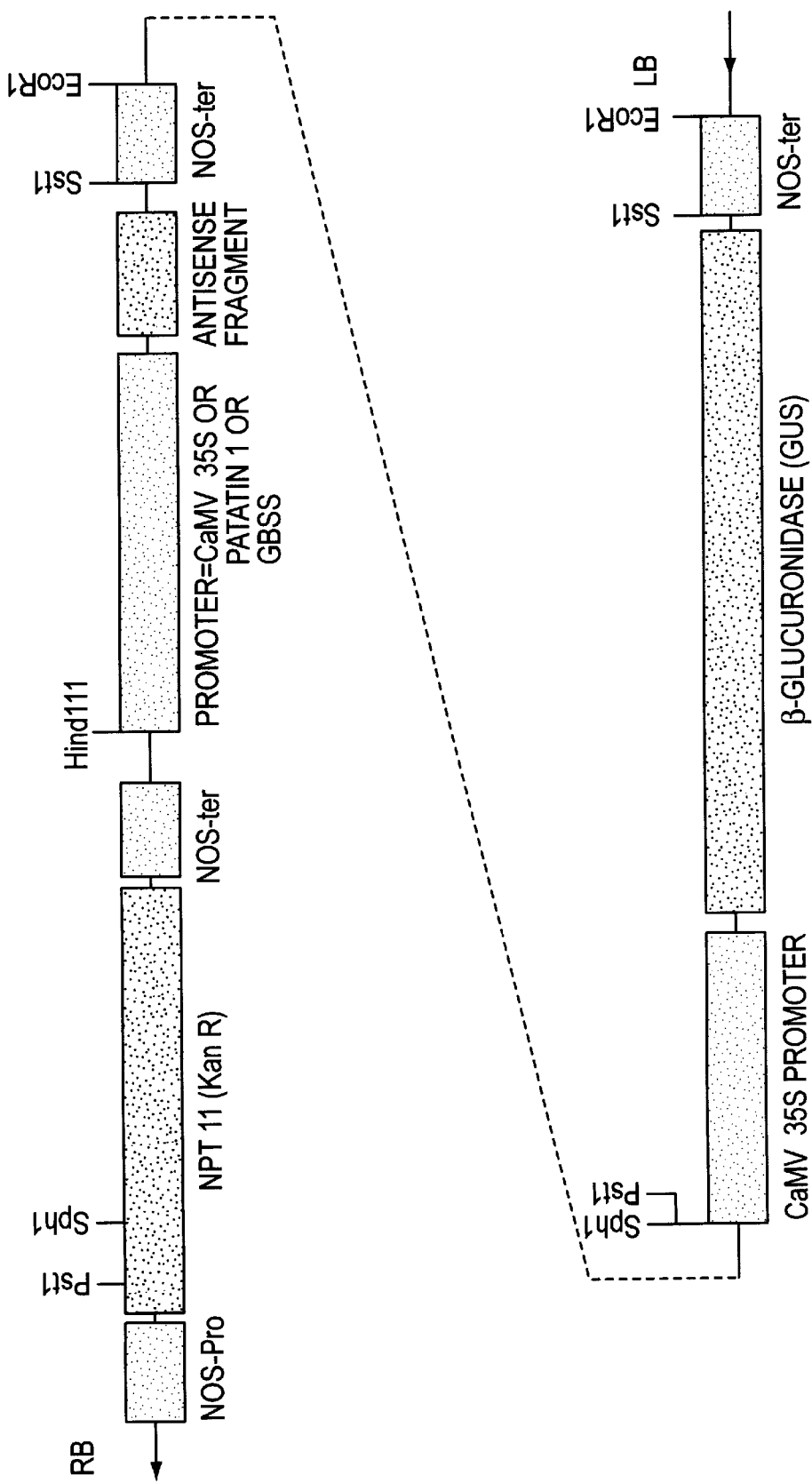

The invention will now be described in more detail with reference to the accompanying figures in which FIG. 1 illustrates the principle of the antisense gene inhibition, and FIG. 2 shows antisense constructs according to the invention (SEQ ID No: 2) (according to Bevan, 1984).

Moreover, the sequence of a tuber-specific promoter is shown in SEQ ID No. 1.

Isolation of Genomic BE Gene in Potato

Based on a known peptide sequence from the BE gene in potato, two synthetic oligo nucleotides overlapping one another are produced. The oligo nucleotides (produced at the Institute for Cell Biology, Uppsala, Sweden, at the applicant's request) are used for identification of cDNA clones from a cDNA library in lambda gt 11 (produced on the applicant's behalf by Clontech, USA). The cDNA clones are used for isolation of the genomic BE gene from a genomic library in EMBL 3 (produced on the applicant's behalf by Clontech, USA).

Antisense Constructs

A varying increase of the amylose content in potato tubers is desired, and therefore different types of antisense genes are constructed which more or less inhibit the expression of the BE gene in vivo. One starts from the isolated genomic BE gene, whereby the antisense constructs comprise parts of the BE gene corresponding to sequences in the region of the promoter, transcription start and the first exon.

In order to obtain both variation of the amylose content and tissue specificity, i.e. the production of amylopectin should be reduced in the potato tuber only, different tuber-specific promoters are coupled to the antisense gene. In addition to the own BE promoter of the tuber, the following promoters are used in different combinations: 35S CaMV, patatin I (obtained from Dr M. Bevan, England) and the potato GBSS promoter.

Isolation and characterization of the potato GBSS gene is described in the simultaneously filed patent application having the title "Genetically engineered modification of potato to form amylopectin-type starch" by the same applicant, and its nucleotide sequence is shown in SEQ ID No. 1. The GBSS promoter is included in the potato gene coding for formation of granule-bound starch synthase. This is the enzyme which mainly is responsible for the formation of amylose in potato.

The binary Ti plasmids pBI 121 and pBI 101 (supplied by Clontech, USA) are used as a basis for all gene structures (FIG. 2), which means that NPT-II and the GUS gene are selection markers. The GUS gene is the gene which codes for beta-glucuronidase.

Transformation

The antisense constructs are transferred to bacteria, suitably by the "freeze-thawing" method (An et al, 1988). The transfer of the recombinant bacterium to potato tissue occurs by incubation of the potato tissue with the recombinant bacterium in a suitable medium after some sort of damage has been inflicted upon the potato tissue. During the incubation, T-DNA from the bacterium enters the DNA of the host plant. After the incubation, the bacteria are killed and the potato tissue is transferred to a solid medium for callus induction and is incubated for growth of callus.

After passing through further suitable media, sprouts are formed which are cut away from the potato tissue.

As a first check that the antisense constructs have been transferred to the potato tissue, this is analyzed regarding the presence of the used marker.

Further checks for testing the expression of the antisense constructs and the transfer thereof to the potato genome are carried out by e.g. southern and northern hybridization (Maniatis et al (1982)). The number of copies of the antisense construct which has been transferred is determined by southern hybridization.

The testing of the expression on protein level is suitably carried out on microtubers induced in vitro on the transformed sprouts, thus permitting the testing to be performed as quickly as possible.

Characterization of the Starch

The composition of the starch in microtubers is identical with that of ordinary potato tubers, and therefore the effect of the antisense constructs on the amylopectin production is examined in microtubers. The proportion of amylose to amylopectin can be determined by a spectrophotometric method (e.g. according to Hovenkamp-Hermelink et al, 1988).

Extraction of Amylose from Amylose Potato

Amylose is extracted from the so-called amylose potato (potato in which the formation of amylopectin has been suppressed to a varying extent by inserting the antisense constructs according to the invention) in a known manner.

Derivatization of Amylose

Depending on the final use of the amylose, its physical and chemical qualities can be modified by derivatization. By derivatization is here meant chemical, physical and enzymatic treatment and combinations thereof (modified starches).

The chemical derivatization, i.e. chemical modification of the amylose, can be carried out in different ways, for example by oxidation, acid hydrolysis, cationization, different forms of etherification, such as cationization, hydroxy propylation and hydroxy ethylation, different forms of esterification, for example by vinyl acetate, acetic anhydride, or by monophosphatizing, diphosphatizing and octenyl succination, and combinations thereof.

Physical modification of the amylose can be effected by e.g. cylinder-drying or extrusion.

In enzymatic derivatization, degradation (reduction of the viscosity) and chemical modification of the amylose are effected by means of existing enzymatic systems.

The derivatization is effected at different temperatures, according to the desired end product. The ordinary range of temperature which is used is 20°–45° C., but temperatures up to 180° C. are possible.

The invention will be described in more detail in the hollowing Examples.

EXAMPLE 1

Production of microtubers with inserted antisense constructs according to the invention The antisense constructs (see FIG. 2) are transferred to Agrobacterium tumefaciens LBA 4404 by the "freeze-thawing" method (An et al, 1988). The transfer to potato tissue is carried out according to a modified protocol from Rocha-Sosa et al (1989).

Leaf discs from potato plants cultured in vitro are incubated in darkness on a liquid MS-medium (Murashige & Skoog; 1962) with 3% saccharose and 0.5% MES together with 100 µl of a suspension of recombinant Agrobacterium per 10 ml medium for two days. After these two days the bacteria are killed. The leaf discs are transferred to a solid medium for callus induction and incubated for 4–6 reeks, depending on the growth of callus. The solid medium is composed as follows:

MS+3% saccarose
- 2 mg/l zeatin riboside
- 0.02 mg/l "NAA"
- 0.02 mg/l "$GA_3$"
- 500 mg/l "Claforan"
- 50 mg/l kanamycin
- 0.25% "Gellan"

Subsequently the leaf discs are transferred to a medium having a different composition of hormones, comprising:

MS+3% saccarose
- 5 mg/l "NAA"
- 0.1 mg/l "BAP"
- 500 mg/l "Claforan"
- 50 mg/l kanamycin
- 0.25% "Gellan"

The leaf discs are stored on this medium for about 4 weeks, whereupon they are transferred to a medium in which the "Claforan" concentration has been reduced to 250 mg/l. If required, the leaf discs are then moved to a fresh medium every 4 or 5 weeks. After the formation of sprouts, these are cut away from the leaf discs and transferred to an identical medium.

The condition that the antisense construct has been transferred to the leaf discs is first checked by analyzing the presence of the GUS gene. Leaf extracts from the regenerated sprouts are analyzed in respect of glucuronidase activity by means of the substrates described by Jefferson et al (1987). The acitivity is demonstrated by visual assessment.

Further tests of the expression of the antisense constructs and the transfer thereof to the potato genome are carried out by southern and northern hybridization according to Maniatis et al (1982). The number of copies of the antisense constructs that has been transferred is determined by southern hybridization.

When it has been established that the antisense constructs have been transferred to and expressed in the potato genome, the testing of the expression on protein level begins. The testing is carried out on microtubers which have been induced in vitro on the transformed sprouts, thereby avoiding the necessity of waiting for the development of a complete potato plant with potato tubers.

Stem pieces of the potato sprouts are cut off at the nodes and placed on a modified MS medium. There they form microtubers after 2–3 weeks in incubation in darkness at 19° C. (Bourque et al, 1987). The medium is composed as follows:

MS+6% saccharose
- 2.5 mg/l kinetin
- 2.5 mg/l "Gellan"

The effect of the antisense constructs on the function of the BE gene in respect of the activity of the BE protein is analysed by means of electrophoresis on polyacrylamide gel (Hovenkamp-Hermelink et al, 1987). Starch is extracted from the microtubers and analysed regarding the presence of the BE protein.

The composition of the starch, i.e. the proportion of amylose to amylopectin, is determined by a spectrophotometric method according to Hovenkamp-Hermelink et al (1988), the content of each starch component being determined on the basis of a standard graph.

EXAMPLE 2

Extraction of amylose from amylose potato.

Potato whose main starch component is amylose, below called amylose potato, modified in a genetically engineered manner according to the invention, is grated, thereby releasing the starch from the cell walls.

The cell walls (fibres) are separated from fruit juice and starch in centrifugal screens (centrisiler). The fruit juice is separated from the starch in two steps, viz. first in hydrocyclones and subsequently in specially designed band-type vacuum filters.

Then a finishing refining is carried out in hydrocyclones in which the remainder of the fruit juice and fibres are separated.

The product is dried in two steps, first by predrying on a vacuum filter and subsequently by final drying in a hot-air current.

EXAMPLE 3

Chemical derivatization of amylose

Amylose is sludged in water to a concentration of 20–50%. The pH is adjusted to 10.0–12.0 and a quaternary ammonium compound is added in such a quantity that the end product obtains a degree of substitution of 0.004–0.2. The reaction temperature is set at 20°–45° C. When the reaction is completed, the pH is adjusted to 4–8, whereupon the product is washed and dried. In this manner the cationic starch derivative 2-hydroxy-3-trimethyl ammonium propyl ether is obtained.

EXAMPLE 4

Chemical derivatization of amylose

Amylose is sludged in water to a water content of 10–25% by weight. The pH is adjusted to 10.0–12.0, and a quaternary ammonium compound is added in such a quantity that the end product obtains a degree of substitution of 0.004–0.2. The reaction temperature is set at 20°–45° C. When the reaction is completed, the pH is adjusted to 4–8. The end product is 2-hydroxy-3-trimethyl ammonium propyl ether.

EXAMPLE 5

Chemical derivatization of amylose

Amylose is sludged in water to a concentration of 20–50% by weight. The pH is adjusted to 5.0–12.0, and sodium hypochlorite is added so that the end product obtains the desired viscosity. The reaction temperature is set at 20°–45° C. When the reaction is completed, the pH is adjusted to 4–8, whereupon the end product is washed and dried. In this manner, oxidized starch is obtained.

EXAMPLE 6

Physical derivatization of amylose

Amylose is sludged in water to a concentration of 20–50% by weight, whereupon the sludge is applied to a heated cylinder where it is dried to a film.

EXAMPLE 7

Chemical and physical derivatization of amylose

Amylose is treated according to the process described in one of Examples 3–5 for chemical modification and is then further treated according to Example 6 for physical derivatization.

REFERENCES

Blennow, A. & Johansson;, G., 1990. Phytochemistry (in press)

De Vries Kuranda, K., 1987. Immunological characterization of normal and amylose-extender alleles of Zea mays L.: Effects on the starch branching enzymes. Thesis for a doctorate. The Pennsylvania State University.

Mac Donald, F. D. & Preiss, J., 1985. Plant Physiol 78:849–852.

Preiss, J., 1988. In Biochemistry of Plants: 14 (Carbohydrates) Ed. J. Preiss, Academic Press; 181–254.

Smith, A., 1988. Plant 175:270–279.

Vos-Scheperkeuter, G. H., de Wit, J. G., Ponstein, A. S., Feenstra, W. J. & Witholt, B., 1989. Plant Physiol 90:75–84.

Cornelissen, M., 1989. Nucleic Acids Res 17(18): 7203–7209.

Izant, J. G., 1989. Cell Motility and Cytosceleton 14:81–91.

Sheehy, R. E., Kramer, M., Hiatt, W. R., 1988. Proc. Natl. Acad. Sci., USA, 85(23):8805–8809.

Van der Krol, A. R., Mur, L. A., de Lange,, P., Gerats, A. G. M., Mol, J. N. M. & Stuitje, A. R., 1990. Mol. Gen. Genet. 220:204–212.

An, G., Ebert, P. R., Mitra, A. & Ha, S. B., 1988. Plant Mol Biol. Manual A3:1–19.

Murashige, T. & Skoog, F., 1962. Physiol. Plant 15:473–497.

Rocha-Sosa, M., Sonnewald, U., Frommer, W., Stratmann, M., Shell, J. & Willmitzer, L., 1989. EMBO J. 8(1):23–29.

Jefferson, R. A., Kavanagh, R. A. & Bevan, M. W., 1987. EMBO J. 6:3901–3907.

Maniatis, T., Fritsch, E. F. & Sambrock, J., 1982. Molecular Cloning. A Laboratory Handbook. Cold Spring Harbor Laboratory Press, Cold Spring Harbor.

Bourque, J. E., Miller, J. C. & Park, W. D., 1987. In Vitro Cellular & Development Biology 23(5):381–386.

Hovenkamp-Hermelink, J. H. M., de Vries, J. N., Adamse, P., Jacobsen, E., Witholt, B. & Feenstra, W. J., 1988. Potato Research 31:241–246.

Modified starches: Properties and use, D. B. Wurzburg.

Bevan, M. W., 1984. Nucleic Acids Res. 12:8711–8721.

SEQ ID No. 1

Sequenced molecule: genomic DNA
Name: Promoter for the GBSS gene from potato
Length of sequence: 629 bp

| | | | | | |
|---|---|---|---|---|---|
| AACCATCCTT | CCTTTTAGCA | GTGTATCAAT | TTTGTAATAG | AACCATGCAT | 50 |
| ACTCAATCTT | AATACTAAAA | TGCAACTTAA | TATAGGCTAA | ACCAAGTAAA | 100 |
| GTAATGTATT | CAACCTTTAG | AATTGTGCAT | TCATAATTAG | ATCTTGTTTG | 150 |
| TCGTAAAAAA | TTAGAAAATA | TATTTACAGT | AATTTGGAAT | ACAAAGCTAA | 200 |
| GGGGGAAGTA | ACTAATATTC | TAGTGGAGGG | AGGGACCAGT | ACCAGTACCT | 250 |
| AGATATTATT | TTTAATTACT | ATAATAATAA | TTTAATTAAC | ACGAGACATA | 300 |
| GGAATGTCAA | GTGGTAGCGT | AGGAGGGAGT | TGGTTTAGTT | TTTTAGATAC | 350 |
| TAGGAGACAG | AACCGGACGG | CCCATTGCAA | GGCCAAGTTG | AAGTCCAGCC | 400 |
| GTGAATCAAC | AAAGAGAGGG | CCCATAATAC | TGTCGATGAG | CATTTCCCTA | 450 |
| TAATACAGTG | TCCACAGTTG | CCTTCTGCTA | AGGGATAGCC | ACCCGCTATT | 500 |
| CTCTTGACAC | GTGTCACTGA | AACCTGCTAC | AAATAAGGCA | GGCACCTCCT | 550 |
| CATTCTCACT | CACTCACTCA | CACAGCTCAA | CAAGTGGTAA | CTTTTACTCA | 600 |
| TCTCCTCCAA | TTATTCTGA | TTTCATGCA | | | 629 |

We claim:

1. Amylose-type starch obtained from a potato by a process comprising introducing into the genome of a potato tissue a gene construct comprising a fragment of the potato gene comprising a transcription start and first exon of the gene coding for formation of branching enzyme (BE gene) inserted in the antisense direction, together with a tuber-specific promoter.

2. The starch according to claim 1, wherein said starch is modified by derivatization.

3. The starch according to claim 2, wherein said derivatization is selected from the group consisting of chemical, physical and enzymatic treatment, and combinations thereof.

4. The starch according to claim 3, wherein the chemical derivatization is selected from the group consisting of oxidation, acid hydrolysis, dextrinization, etherification, esterification, and combinations thereof.

5. The starch according to claim 4, wherein the etherification is selected from the groups consisting of cationization, hydroxy propylation and hydroxy ethylation.

6. The starch according to claim 5, wherein the esterification is selected from the group consisting of vinyl acetate esterification, acetic anhydride esterification and monophosphatizing, diphosphatizing and octenyl succination.

7. The starch according to claim 3, wherein the starch is physically modified by cylinder-drying or extrusion.

8. The starch according to claim 3, wherein the starch is enzymatically derivatized by degradation (reduction of the viscosity) and chemical modification of the starch.

9. The starch according to claim 2, wherein the derivatization is effected at a temperature of from 20°–45° C.

10. A food additive comprising the starch according to claim 7.

* * * * *